United States Patent [19]

Li

[11] Patent Number: 5,316,690

[45] Date of Patent: May 31, 1994

[54] HYDROCHLOROFLUOROCARBONS HAVING OH RATE CONSTANTS WHICH DO NOT CONTRIBUTE SUBSTANTIALLY TO OZONE DEPLETION AND GLOBAL WARMING

[75] Inventor: Chien C. Li, Erie, N.Y.

[73] Assignee: Allied Signal Inc., Morristownship, Morris County, N.J.

[21] Appl. No.: 746,449

[22] Filed: Aug. 16, 1991

Related U.S. Application Data

[63] Continuation-in-part of Ser. No. 687,342, Apr. 18, 1991, Pat. No. 5,158,617.

[51] Int. Cl.$^5$ .......................... C07C 19/08; C11D 7/30; C11D 7/50
[52] U.S. Cl. ........................................ 252/172; 8/142; 134/40; 252/67; 252/162; 252/194; 252/364; 264/53; 521/98; 521/131
[58] Field of Search ................. 570/134; 252/67, 162, 252/172, 364, 194; 134/40; 264/53; 8/142; 521/98, 131

[56] References Cited

U.S. PATENT DOCUMENTS

| | | | |
|---|---|---|---|
| 2,582,242 | 1/1952 | Eberl | 128/90 |
| 2,683,093 | 7/1954 | Eberl | 252/364 |
| 3,332,840 | 7/1967 | Regan | 570/134 |
| 3,431,313 | 3/1969 | Regan | 570/134 |
| 3,444,249 | 5/1969 | Regan | 570/134 |
| 4,947,881 | 8/1990 | Magid et al. | 134/40 |
| 4,954,666 | 9/1990 | Bielefeldt et al. | 570/134 |
| 4,985,168 | 1/1991 | Ohmure et al. | 252/67 |
| 5,034,149 | 7/1991 | Merchant | 252/171 |
| 5,158,617 | 10/1992 | Li | 134/40 |

FOREIGN PATENT DOCUMENTS

| | | | |
|---|---|---|---|
| 347926 | 12/1989 | European Pat. Off. | |
| 2221386 | 9/1990 | Japan | 252/172 |
| 2222494 | 9/1990 | Japan | 252/172 |
| 9008814 | 8/1990 | PCT Int'l Appl. | |

OTHER PUBLICATIONS

Henne et al "Fluorinated Derivatives of Propane" Parts I–IV, *J.A.C.S.* vol. 59, pp. 2434–2436 *(1937); vol. 60 pp. 2491–2495 *(1938); vol. 61 pp. 2489–2491 *(1939); vol. 63 pp. 3476–3477 *(1941).

Robbins *Journal of Pharmacology and Experimental Therapeutics* vol. 86 Feb. 1946 pp. 197–204.

Kunshenko et al. Translation of *Zh. Org. Khim.* vol. 24, No. 4 (pp. 705–713) Apr. 1988 by Plenum Publishing Corp. ©1988 pp. 633–640.

Sheremet'ev et al Translation of *Zh. Obshch. Khim.* vol. 59 No. 3 (pp. 631–636) Mar. 1989 by Plenum Publishing Corp. ©1989 pp. 559–563.

Chemical Abstract CA 115: 210719K, Abstract of Japanese Patent 03-123743 (May/1991.)

*Federal Register* vol. 56, No. 14 Jan. 22, 1991 pp. 2420–2424.

Chemical Abstract, vol. 114, No. 10, Mar. 11, 1991 Abstract No. 84384m.

Chemical Abstracts, vol. 114, No. 10, Mar. 11, 1991 Abstract No. 84385n.

Addition of Free of Free Radicals to Unsaturated Systems R. N. Haszeldine and B. R. Steele pp. 2193–2197 *1957.

Atkinson, Chem. Rev. 86, 69 (1986)*.

Taylor et al., Int. J. of Chem. Kinetics 21, 829 (1989)*.

*Primary Examiner*—Linda Skaling
*Attorney, Agent, or Firm*—Karen A. Harding; Jay P. Friedenson

[57] ABSTRACT

The present invention provides hydrochlorofluorocarbons having 3 to 5 carbons atoms, 1 to 2 chlorine atoms, and an OH rate constant from about 8 to about 25 cm$^3$/molecule/sec $\times 10^{-14}$. The hydrochlorofluorocarbons are useful as solvents and blowing agents.

6 Claims, No Drawings

HYDROCHLOROFLUOROCARBONS HAVING OH RATE CONSTANTS WHICH DO NOT CONTRIBUTE SUBSTANTIALLY TO OZONE DEPLETION AND GLOBAL WARMING

This application is a continuation-in-part patent application of patent application Ser. No. 687,342 filed Apr. 18, 1991, now U.S. Pat. No. 3,158,617.

BACKGROUND OF THE INVENTION

The present invention relates to a class of hydrochlorofluorocarbons which have 3 to 5 carbon atoms, have 1 to 2 chlorine atoms, and have OH rate constants from about 8 to about 25 cm$^3$/molecule/sec × 10−14.

Vapor degreasing and solvent cleaning with fluorocarbon based solvents have found widespread use in industry for the degreasing and otherwise cleaning of solid surfaces, especially intricate parts and difficult to remove soils.

In its simplest form, vapor degreasing or solvent cleaning consists of exposing a room-temperature object to be cleaned to the vapors of a boiling solvent. Vapors condensing on the object provide clean distilled solvent to wash away grease or other contamination. Final evaporation of solvent from the object leaves behind no residue as would be the case where the object is simply washed in liquid solvent.

For soils which are difficult to remove, where elevated temperature is necessary to improve the cleaning action of the solvent, or for large volume assembly line operations where the cleaning of metal parts and assemblies must be done efficiently and quickly, the conventional operation of a vapor degreaser consists of immersing the part to be cleaned in a sump of boiling solvent which removes the bulk of the soil, thereafter immersing the part in a sump containing freshly distilled solvent near room temperature, and finally exposing the part to solvent vapors over the boiling sump which condense on the cleaned part. In addition, the part can also be sprayed with distilled solvent before final rinsing.

Vapor degreasers suitable in the above-described operations are well known in the art. For example, Sherliker et al. in U.S. Pat. No. 3,085,918 disclose such suitable vapor degreasers comprising a boiling sump, a clean sump, a water separator, and other ancilliary equipment.

Cold cleaning is another application where a number of solvents are used. In most cold cleaning applications, the soiled part is either immersed in the fluid or wiped with rags or similar objects soaked in solvents.

In cold cleaning applications, the use of the aerosol packaging concept has long been found to be a convenient and cost effective means of dispensing solvents. Aerosol products utilize a propellant gas or mixture of propellant gases, preferably in a liquefied gas rather than a compressed gas state, to generate sufficient pressure to expel the active ingredients, i.e. product concentrates such as solvents, from the container upon opening of the aerosol valve. The propellants may be in direct contact with the solvent, as in most conventional aerosol systems, or may be isolated from the solvent, as in barrier-type aerosol systems.

Chlorofluorocarbon solvents, such as trichlorotrifluoroethane, have attained widespread use in recent years as effective, nontoxic, and nonflammable agents useful in degreasing applications and other solvent cleaning applications. Trichlorotrifluoroethane has been found to have satisfactory solvent power for greases, oils, waxes and the like. It has therefore found widespread use for cleaning electric motors, compressors, heavy metal parts, delicate precision metal parts, printed circuit boards, gyroscopes, guidance systems, aerospace and missile hardware, aluminum parts and the like. Trichlorotrifluoroethane has two isomers: 1,1,2-trichloro-1,2,2-trifluoroethane (known in the art as CFC-113) and 1,1,1-trichloro-2,2,2-trifluoroethane (known in the art as CFC-113a). CFC-113 has a boiling point of about 470° C. and has been found to have satisfactory solvent power for greases, oils, waxes, and the like.

Another commonly used solvent is chloroform (known in the art as HCC-20) which has a boiling point of about 630° C. Perchloroethylene is a commonly used dry cleaning and vapor degreasing solvent which has a boiling point of about 121° C. These compounds are disadvantageous for use as solvents because they are toxic; also, chloroform causes liver damage when inhaled in excess.

Although chlorine is known to contribute to the solvency capability of a compound, fully halogenated chlorofluorocarbons and hydrochlorofluorocarbons are suspected of causing environmental problems in connection with the earth's protective ozone layer. Thus, the art is seeking new compounds which do not contribute to environmental problems but yet provide the solvency properties of CFC-113.

Chlorofluorocarbons (CFCS) such as CFC-113 are suspected of causing environmental problems in connection with the ozone layer. Under the Clean Air Act, CFC-113 is being phased-out of production.

In response to the need for stratospherically safe materials, substitutes have been developed and continue to be developed. *Research Disclosure* 14623 (June 1978) reports that 1,1-dichloro-2,2,2-trifluoroethane (known in the art as HCFC-123) is a useful solvent for degreasing and defluxing substrates. In the EPA "Findings of the Chlorofluorocarbon Chemical Substitutes International Committee", EPA-600/9-88-009 (April 1988), it was reported that HCFC-123 and 1,1-dichloro-1-fluoroethane (known in the art as HCFC-141b) have potential as replacements for CFC-113 as cleaning agents.

The problem with these substitutes is that they have a long atmospheric lifetime as determined by their reaction with OH radicals in the troposphere. Table I below contains the OH rate constants and corresponding atmospheric lifetimes for these substitutes. In Table I, Exp $K_{OH}$ stands for experimental $K_{OH}$ rate constant, Est $K_{OH}$ stands for estimated $K_{OH}$ rate constant, Exp Life stands for experimental lifetime, and Est Life stands for estimated lifetime. The unit on the rate constant is cm$^3$/molecule/sec × 10−14 and the unit on the lifetime is years.

TABLE I

| Number | Formula | Exp $K_{OH}$ | Est $K_{OH}$ | Exp Life | Est Life |
|---|---|---|---|---|---|
| HCFC-123 | CHCl$_2$CF$_3$ | 3.7 | 2.96 | 2.0 | 2.6 |
| HCFC-124 | CF$_3$CHClF | 1.0 | 1.00 | 7.5 | 7.5 |
| HCFC-141b | CFCl$_2$CH$_3$ | 0.75 | 2.10 | 10.1 | 3.6 |
| HCFC-142b | CF$_2$ClCH$_3$ | 0.38 | 2.10 | 19.9 | 6 |
| HCFC-225ca | CF$_3$CF$_2$CHCl$_2$ | 2.49 | 3.30 | 2.3 | 2.3 |
| HCFC-225cb | CClF$_2$CF$_2$CHClF | 0.91 | 3.86 | 2 | 1.96 |
| HCC-140 | CCl$_3$CH$_3$ | 1.2 | 1.21 | 6.3 | 6.3 |

It would be desirable to have substitutes with OH rate constants of at least about 8 cm$^3$/molecule/sec$\times 10^{-14}$ which equates to an atmospheric lifetime of 12 months or less.

If the OH rate constant of a compound is too high, the compound is a VOC (Volatile Organic Compound) because it is so reactive that it forms carbon dioxide which contributes to global warming. Thus, it would be desirable to have substitutes with OH rate constants of 25 cm$^3$/molecule/sec$\times 10^{-14}$ or less which equates to an atmospheric lifetime of at least 4 months.

Commonly assigned U.S. Pat. No. 4,947,881 teaches a method of cleaning using hydrochlorofluoropropanes having 2 chlorine atoms and a difluoromethylene group. European Publication 347,924 published Dec. 27, 1989 teaches hydrochlorofluoropropanes having a difluoromethylene group. International Publication Number WO 90/08814 published Aug. 9, 1990 teaches azeotropes having at least one hydrochlorofluoropropane having a difluoromethylene group.

A wide variety of consumer parts is produced on an annual basis in the United States and abroad. Many of these parts have to be cleaned during various manufacturing stages in order to remove undesirable contaminants. These parts are produced in large quantities and as a result, substantial quantities of solvents are used to clean them.

Thus, substitutes having OH rate constants between about 8 and about 25 cm$^3$/molecule/sec$\times 10^{-14}$ and which are useful in many applications including as solvents are needed in the art.

SUMMARY OF THE INVENTION

Straight chain and branched chain hydrochlorofluorocarbons having 3 to 5 carbon atoms and 1 or 2 chlorine atoms total over 1100 compounds. Out of this over 1100 compounds, I was surprised to find a class of 88 hydrochlorofluorocarbons having OH rate constants from about 8 to about 25 cm$^3$/molecule/sec$\times 10^{31\ 14}$.

The OH rate constant can be determined by any method known in the art. For example, see Atkinson, "Kinetics and Mechanisms of the Gas-Phase Reactions of the Hydroxyl Radical with Organic Compounds under Atmospheric Conditions", *Chem. Rev.*, 86, 69 (1986) and Taylor et al., "Laser Photolysis/Laser-Induced Fluorescence Studies of Reaction Rates of OH with CH$_3$Cl, CH$_2$Cl$_2$, and CHCl$_3$ over an Extended Temperature Range", *Int. J. of Chem, Kinetics* 21, 829 (1989).

The straight chain hydrochlorofluorocarbons having 3 carbon atoms of the present invention are listed in Table II below. The unit on the calculated K$_{OH}$ is cm$^3$/molecule/sec$\times 10^{-14}$ and the unit on the calculated lifetime is years in Table II.

TABLE II

| Number | Chemical Formula | K$_{OH}$ | Lifetime |
|---|---|---|---|
| HCFC-234aa | CF$_2$HCCl$_2$CF$_2$H | 24.5 | 0.30 |
| HCFC-234ab | CFH$_2$CCl$_2$CF$_3$ | 11.9 | 0.64 |
| HCFC-234ba | CF$_2$HCFClCFClH | 22.9 | 0.33 |
| HCFC-234bb | CF$_3$CFClCClH$_2$ | 9.5 | 0.80 |
| HCFC-234bc | CFH$_2$CFClCF$_2$Cl | 13.1 | 0.58 |
| HCFC-234fa | CF$_2$ClCH$_2$CF$_2$Cl | 8.2 | 0.92 |
| HCFC-234fb | CF$_3$CH$_2$CFCl$_2$ | 8.2 | 0.92 |
| HCFC-243ea | CFClHCFHCFClH | 19.1 | 0.40 |
| HCFC-243ec | CF$_2$ClCFHCClH$_2$ | 8.4 | 0.90 |
| HCFC-244ba | CFH$_2$CFClCF$_2$H | 12.0 | 0.63 |
| HCFC-244da | CF$_2$HCClHCF$_2$H | 11.85 | 0.64 |
| HCFC-244db | CF$_3$CClHCFH$_2$ | 9.3 | 0.81 |
| HCFC-244ea | CF$_2$HCFHCFClH | 11.9 | 0.64 |

TABLE II-continued

| Number | Chemical Formula | K$_{OH}$ | Lifetime |
|---|---|---|---|
| HCFC-244eb | CF$_3$CFHCClH$_2$ | 10.5 | 0.72 |
| HCFC-244ec | CFH$_2$CFHCF$_2$Cl | 10.1 | 0.75 |
| HCFC-244fa | CFClHCH$_2$CF$_3$ | 8.5 | 0.89 |
| HCFC-244fb | CF$_2$HCH$_2$CF$_2$Cl | 9.15 | 0.83 |
| HCFC-252dc | CH$_3$CClHCF$_2$Cl | 15.3 | 0.49 |
| HCFC-252ec | CH$_3$CFHCCl$_2$F | 8.6 | 0.88 |
| HCFC-253ba | CFH$_2$CFClCFH$_2$ | 17.7 | 0.43 |
| HCFC-253bb | CH$_3$CFClCF$_2$H | 13.8 | 0.55 |
| HCFC-253ea | CF$_2$HCFHCClH$_2$ | 14.5 | 0.52 |
| HCFC-253eb | CClFHCFHCFH$_2$ | 16.5 | 0.46 |
| HCFC-253ec | CH$_3$CFHCF$_2$Cl | 8.0 | 0.95 |
| HCFC-253fa | CF$_2$HCH$_2$CFClH | 14.5 | 0.52 |
| HCFC-253fc | CFH$_2$CH$_2$CF$_2$Cl | 11.5 | 0.66 |
| HCFC-262fa | CF$_2$HCH$_2$CClH$_2$ | 14.99 | 0.50 |
| HCFC-262fb | CFH$_2$CH$_2$CFClH | 17.8 | 0.43 |
| HCFC-271b | CH$_3$CFClCH$_3$ | 9.95 | 0.76 |
| HCFC-271d | CH$_3$CClHCFH$_2$ | 19.44 | 0.39 |
| HCFC-271fb | CH$_3$CH$_2$CFClH | 9.98 | 0.76 |

This present class with its OH rate constants between about 8 to about 25 cm$^3$/molecule/sec$\times 10^{-14}$ unexpected. I discovered this when I compared isomers having the same —CAB—group wherein —CAB— is —CCl$_2$—, —CH$_2$—, —CClH—, —CClF—, and —CHF—as the covered compound. I found that the isomers had OH rate constants less than 8 or greater than 25 cm$^3$/molecule/sec$\times 10^{-14}$. For example, CFClHCFHCFClH and CF$_2$ClCFHCClH$_2$ of the present invention have K$_{OH}$ values of 19.1 and 8.4 cm$^3$/molecule/sec$\times 10^{-14}$ respectively as shown in Table II. In contrast, the isomers, CF$_2$HCFHCCl$_2$H and CCl$_2$FCFHCFH$_2$, have K$_{OH}$ values of 31.3 and 30.0 cm$^3$/molecule/sec$\times 10^{-14}$ respectively as shown in Table VII, and thus, are VOCs.

Also, CFH$_2$CFClCF$_2$H of the present invention has a K$_{OH}$ of 12.0 cm$^3$/molecule/sec$\times 10^{-14}$ as shown in Table II. In contrast, the isomer, CF$_3$CFClCH$_3$, has a K$_{OH}$ of 1.8 cm$^3$/molecule/sec$\times 10^{-14}$ as shown in Table VII, and thus, has a long atmospheric lifetime. The isomers, CFH$_2$CCl$_2$CFH$_2$ and CH$_3$CCl$_2$CF$_2$H, have K$_{OH}$ values of 49.33 and 34.14 cm$^3$/molecule/sec$\times 10^{-14}$ respectively as shown in Table VII and thus, are VOCs.

Additionally, CH$_3$CFHCCl$_2$F of the present invention has a K$_{OH}$ of 8.6 cm$^3$/molecule/sec$\times 10^{-14}$ as shown in Table II. In contrast, the isomers, CClH$_2$CFHCClFH and CFH$_2$CFHCCl$_2$H, have K$_{OH}$ values of 31.8 and 39.57 cm$^3$/molecule/sec$\times 10^{-14}$ respectively as shown in Table VII, and thus, are VOCs.

Additionally, CF$_2$HCH$_2$CClH$_2$ and CFH$_2$CH$_2$CFClH of the present invention have K$_{OH}$ values of 14.99 and 17.8 cm$^3$/molecule/sec$\times 10^{-14}$ respectively as shown in Table II. In contrast, the isomer, CF$_2$ClCH$_2$CH$_3$, has a K$_{OH}$ of 2.9 cm$^3$/molecule/sec$\times 10^{-14}$ as shown in Table VII, and thus, has a long atmospheric lifetime. Additionally, CH$_3$CH$_2$CFClH of the present invention has a K$_{OH}$ of 9.98 cm$^3$/molecule/sec$\times 10^{-14}$ as shown in Table II. In contrast, the isomer, CFH$_2$CH$_2$CClH$_2$, has a K$_{OH}$ value of 35.8 cm$^3$/molecule/sec$\times 10^{-14}$ as shown in Table VII, and thus, is a VOC.

Known methods for making fluorinated compounds can be modified in order to form the straight chain hydrochlorofluorocarbons having 3 carbon atoms of the present invention.

For example, Haszeldine, *Nature* 165, 152 (1950) teaches the reaction of trifluoroiodomethane and acetylene to prepare 3,3,3-trifluoro-1-iodopropene which is then dehydroiodinated to form 3,3,3-trifluoropropyne. By using 3,3,3-trifluoropropyne as a starting material, $CF_3CFClCClH_2$ (HCFC-234bb) may be prepared as follows. Commercially available trifluoromethyl iodide may be reacted with acetylene to prepare 3,3,3-trifluoro-1-iodopropene which is then dehydroiodinated to form 3,3,3-trifluoropropyne. The 3,3,3-trifluoropropyne may then be reacted with commercially available hydrogen fluoride to form 2,3,3,3-tetrafluoro-1-propene which is then chlorinated to form 1,2-dichloro-2,3,3,3-tetrafluoropropane.

$CF_2ClCFHCClH_2$ (HCFC-243ec) may be prepared as follows. Commercially available 1,1,3-trichloropropene may be dehydrohalogenated to form 1,3-dichloro-1-propyne. The 1,3-dichloro-1-propyne may then be fluorinated to form 1,3-dichloro-1,2-difluoro-1-propene which may then be reacted with commercially available hydrogen fluoride to form 1,3-dichloro-1,1,2-trifluoropropane.

$CFH_2CFClCF_2H$ (HCFC-244ba) may be prepared as follows. Commercially available 1,3-difluoro-2-propanol may be dehydrated to form 1,3-difluoro-1-propene which may then be dehydrohalogenated to form 3-fluoro-1-propyne. The 3-fluoro-1-propyne may then be fluorinated, chlorinated, and fluorinated to form 1,1,2,3-tetrafluoro-2-chloropropane.

$CFH_2CFHCF_2Cl$ (HCFC-244ec) may be prepared as follows. Commercially available 1,1,3-trichloropropene may be fluorinated to form 1,1-dichloro-3-fluoro-1-propene which may then be dehydrohalogenated to form 1-chloro-3-fluoro-1-propyne. The 1-chloro-3-fluoro-1-propyne may then be fluorinated to form 1-chloro-1,2,3-trifluoro-1-propene which may then be reacted with commercially available hydrogen fluoride to form 1-chloro-1,1,2,3-tetrafluoropropane.

$CFClHCH_2CF_3$ (HCFC-244fa) may be prepared as follows. Commercially available 1,1,3-trichloropropene may be fluorinated to form 1,1,1,2,3-pentafluoropropane. The 1,1,1,2,3-pentafluoropropane may then be dehydrohalogenated to form 1,3,3,3-tetrafluoro-1-propene which may then be reacted with commercially available hydrogen chloride to form 1-chloro-1,3,3,3-tetrafluoropropane.

$CF_2HCH_2CF_2Cl$ (HCFC-244fb) may be prepared as follows. Commercially available 2,2,3,3-tetrafluoro-1-propanol may be fluorinated to form 1,1,1,2,2,3-hexafluoropropane which may then be dehydrohalogenated to form 1,3,3-trifluoro-1-propyne. The 1,3,3-trifluoro-1-propyne may then be reacted with commercially available hydrogen chloride to form 1-chloro-1,3,3-trifluoro-1-propene which may then be reacted with commercially available hydrogen fluoride to form 1-chloro-1,1,3,3-tetrafluoropropane.

$CH_3CFClCF_2H$ (HCFC-253bb) may be prepared as follows. Commercially available 1,2-dibromopropane may be dehydrohalogenated to form propyne. The propyne may then be fluorinated, chlorinated, and fluorinated to form 2-chloro-1,1,2-trifluoropropane.

$CH_3CFHCF_2Cl$ (HCFC-253ec) may be prepared as follows. Commercially available 1,2-dichloropropane may be dehydrohalogenated to form 1-chloro-1-propene which may then be dehydrogenated to form 1-chloro-1-propyne. The 1-chloro-1-propyne may then be reacted with commercially available hydrogen fluoride to form 1-chloro-1-fluoro1-propene which may then be fluorinated to form 1-chloro-1,1,2-trifluoropropane.

The preferred straight chain hydrochlorofluorocarbons having 3 carbon atoms are $CF_2ClCFHCClH_2$, $CFH_2CFClCF_2H$, $CFH_2CFHCF_2Cl$, $CFClHCH_2CF_3$, $CF_2HCH_2CF_2Cl$, $CH_3CFClCF_2H$, and $CH_3CFHCF_2Cl$.

The straight chain hydrochlorofluorocarbons having 4 carbon atoms of the present invention are listed in Table III below. The unit on the calculated $K_{OH}$ is $cm^3/molecule/sec \times 10^{-14}$ and the unit on the calculated lifetime is years in Table III below.

TABLE III

| Number | Chemical Formula | $K_{OH}$ | Lifetime |
|---|---|---|---|
| HCFC-3541cd | $CH_3CClHCF_2CF_2Cl$ | 12.8 | 0.59 |
| HCFC-354mbd | $CH_3CClHCFClCF_3$ | 11.9 | 0.63 |
| HCFC-355lcf | $CFH_2CH_2CF_2CF_2Cl$ | 12.0 | 0.63 |
| HCFC-355lec | $CH_3CF_2CFHCF_2Cl$ | 12.8 | 0.59 |
| HCFC-355lef | $CF_2HCH_2CFHCF_2Cl$ | 15.6 | 0.48 |
| HCFC-355lff | $CF_3CH_2CH_2CF_2Cl$ | 10.4 | 0.73 |
| HCFC-355mbf | $CFH_2CH_2CFClCF_3$ | 11.5 | 0.66 |
| HFFC-355mcf | $CF_3CF_2CH_2CClH_2$ | 8.93 | 0.85 |
| HCFC-355mdc | $CH_3CF_2CClHCF_3$ | 12.0 | 0.63 |
| HCFC-355mdf | $CF_2HCH_2CClHCF_3$ | 14.3 | 0.53 |
| HCFC-355meb | $CH_3CFClCFHCF_3$ | 11.8 | 0.64 |
| HCFC-355med | $CFH_2CClHCFHCF_3$ | 14.1 | 0.54 |
| HCFC-355mfb | $CFH_2CFClCH_2CF_3$ | 15.9 | 0.48 |
| HCFC-355mfc | $CF_3CH_2CF_2CClH_2$ | 13.2 | 0.57 |
| HCFC-355mfd | $CF_2HCClHCH_2CF_3$ | 14.9 | 0.51 |
| HCFC-355mfe | $CFClHCFHCH_2CF_3$ | 15.1 | 0.50 |
| HCFC-355pcb | $CH_3CFClCF_2CF_2H$ | 15.7 | 0.48 |
| HCFC-355rcc | $CH_3CF_2CF_2CFClH$ | 15.2 | 0.50 |
| HCFC-363lbfs | $CH_3CH_2CClFCF_2Cl$ | 13.4 | 0.56 |
| HCFC-364med | $CH_3CClHCFHCF_3$ | 15.0 | 0.50 |
| HCFC-364mff | $CFClHCH_2CH_2CF_3$ | 15.5 | 0.49 |
| HCFC-373lef | $CH_3CH_2CFHCF_2Cl$ | 9.11 | 0.83 |
| HCFC-373mfd | $CH_3CClHCH_2CF_3$ | 14.3 | 0.53 |
| HCFC-373mff | $CF_3CH_2CH_2CClH_2$ | 13.2 | 0.57 |
| HCFC-391rff | $CH_3CH_2CH_2CFClH$ | 10.3 | 0.73 |
| HCFC-391sbf | $CH_3CH_2CFClCH_3$ | 14.2 | 0.53 |

Known methods for making fluorinated compounds can be modified in order to form the straight chain hydrochlorofluorocarbons having 4 carbon atoms of the present invention.

For example, R. N. Haszeldine et al., "Addition of Free Radicals to Unsaturated Systems. Part XIII. Direction of Radical Addition to Chloro-1:1-difluoroethylene", *J. of Amer. Chem. Soc.*, 2193 (1957) teach the reaction of trifluoroiodomethane with chloro-1:1-difluoroethylene to prepare 3-chloro-1:1:1:2:2-pentafluoro-3-iodopropane which is then chlorinated to form 1,1-dichloro-2,2,3,3,3-pentafluoropropane (known in the art as HCFC-225ca). This known method can be modified to form $CF_3CF_2CH_2CClH_2$ (HCFC-355mcf) as follows. Commercially available perfluoroethyl iodide can be reacted with commercially available ethylene to prepare 1,1,1,2,2-pentafluoro-4-iodobutane which is then chlorinated to form 1,1,1,2,2-pentafluoro-4-chlorobutane.

$CH_3CF_2CFHCF_2Cl$ (HCFC-355lec) may be prepared as follows. Commercially available 1,3-dichloro-2-butene may be fluorinated to form 1-chloro-2,3,3-trifluorobutane which may then be dehydrohalogenated to form 1-chloro-3,3-difluoro-1-butene. The 1-chloro-3,3-difluoro-1-butene may then be dehydrogenated to form 1-chloro-3,3-difluoro-1-propyne which may then be fluorinated to form 1-chloro-1,2,3,3-tetrafluoro-1-butene which may then be reacted with commercially available hydrogen fluoride to form 1-chloro-1,1,2,3,3-pentafluorobutane.

$CF_3CH_2CH_2CF_2Cl$ (HCFC-355lff) may be prepared as follows. Commercially available 2,3-dichlorohexafluoro-2-butene may be dechlorinated to form hexafluoro-2-butyne. The hexafluoro-2-butyne may be hydrogenated to form 1,1,1,4,4,4-hexafluorobutane which may be chlorinated to form 1-chloro-1,1,4,4,4-pentafluorobutane.

$CFH_2CH_2CFClCF_3$ (HCFC-355mbf) may be prepared as follows. Commercially available 1,4-dichloro-2-butyne may be reacted with commercially available hydrogen fluoride to form 1,4-dichloro-2-fluoro-2-butene which may be fluorinated to form 1,2,4-trifluoro-2-butene. The 1,2,4-trifluoro-2-butene may be reacted with commercially available hydrogen chloride to form 2-chloro-1,2,4-trifluorobutane which may be dehydrohalogenated, fluorinated, dehydrohalogenated, and fluorinated to form 2-chloro-1,1,1,2,4-pentafluorobutane.

$CH_3CF_2CClHCF_3$ (HCFC-355mdc) may be prepared as follows. Commercially available 3,4-dichloro-1-butene may be dehydrogenated to form 3,4-dichloro-1-butyne which may be reacted with commercially available hydrogen fluoride to form 1,2-dichloro-3,3-difluorobutane. The 1,2-dichloro-3,3-difluorobutane may be dehydrogenated to form 1,2-dichloro-3,3-difluoro-1-butene which may be reacted with commercially available hydrogen fluoride to form 2-chloro-1,1,3,3-tetrafluorobutane. The 2-chloro-1,1,3,3-tetrafluorobutane may be dehydrogenated to form 2-chloro-1,1,3,3-tetrafluoro-1-butene which may be reacted with commercially available hydrogen fluoride to form 2-chloro-1,1,1,3,3-pentafluorobutane.

$CH_3CFClCFHCF_3$ (HCFC-355meb) may be prepared as follows. Commercially available 1,3-dichloro-2-butene may be fluorinated to form 2-chloro-2,3,4-trifluorobutane which may be dehydrohalogenated to form 3-chloro-1,3-difluoro-1-butene. The 3-chloro-1,3-difluoro-1-butene may be fluorinated to form 2-chloro-2,3,4,4-tetrafluorobutane which may be dehydrohalogenated to form 3-chloro-1,1,3-trifluoro-1-butene. The 3-chloro-1,1,3-trifluoro-1-butene may be fluorinated to form 2-chloro-2,3,4,4,4-pentafluorobutane.

$CH_3CFClCF_2CF_2H$ (HCFC-355pcb) may be prepared as follows. Commercially available 1,3-dichloro-2-butene may be fluorinated to form 2-chloro-2,3,4-trifluorobutane which may be dehydrogenated to form 3-chloro-1,2,3-trifluoro-1-butene. The 3-chloro-1,2,3-trifluoro-1-butene may be fluorinated to form 2-chloro-2,3,3,4,4-pentafluorobutane.

$CH_3CF_2CF_2CFClH$ (HCFC-355rcc) may be prepared as follows. Commercially available 1,3-dichloro-2-butene may be fluorinated to form 1-chloro-2,3,3-trifluorobutane which may be dehydrogenated to form 1-chloro-2,3,3-trifluoro-1-butene. The 1-chloro-2,3,3-trifluoro-1-butene may be fluorinated to form 1-chloro-1,2,2,3,3-pentafluorobutane.

$CH_3CClHCFHCF_3$ (HCFC-364med) may be prepared as follows. Commercially available 1,3-dichloro-2-butene may be reacted with commercially available hydrogen fluoride to form 1,3-dichloro-2-fluorobutane which may be dehydrohalogenated to form 1,3-dichloro-1-butene. The 1,3-dichloro-1-butene may be fluorinated to form 2-chloro-3,4,4-trifluorobutane which may be dehydrohalogenated to form 3-chloro-1,1-difluoro-1-butene. The 3-chloro-1,1-difluoro-1-butene may be fluorinated to form 2-chloro-3,4,4,4-tetrafluorobutane.

The preferred straight chain hydrochlorofluorocarbons having 4 carbon atoms are $CH_3CF_2CFHCF_2Cl$, $CF_3CH_2CH_2CF_2Cl$, $CFH_2CH_2CFClCF_3$, $CH_3CF_2CClHCF_3$, $CH_3CFClCF_2CF_2H$, $CH_3CF_2CF_2CFClH$, and $CH_3CClHCFHCF_3$.

The branched chain hydrochlorofluorocarbons having 4 carbon atoms of the present invention are listed in Table IV below. The unit on the calculated $K_{OH}$ is $cm^3/molecule/sec \times 10^{31}$ [14] and the unit on the calculated lifetime is years in Table IV below.

TABLE IV

| Number | Chemical Formula | $K_{OH}$ | Lifetime |
|---|---|---|---|
| HCFC-345kms | $CH_3C(CF_3)FCFCl_2$ | 9.11 | 0.83 |
| HCFC-345lls | $CH_3C(CF_2Cl)FCF_2Cl$ | 9.11 | 0.83 |
| HCFC-355lms | $CH_3C(CF_3)HCF_2Cl$ | 8.3 | 0.91 |
| HCFC-355mop | $CF_2HC(CClH_2)HCF_3$ | 14.5 | 0.52 |
| HCFC-355mps | $CH_3C(CF_2H)ClCF_3$ | 15.3 | 0.50 |
| HCFC-355mrs | $CH_3C(CFClH)FCF_3$ | 15.1 | 0.50 |
| HCFC-373mss | $CH_3C(CH_3)ClCF_3$ | 13.4 | 0.56 |

Known methods for making fluorinated compounds can be modified in order to form the branched hydrochlorofluorocarbons having 4 carbon atoms of the present invention.

$CH_3C(CF_3)HCF_2Cl$ (HCFC-355lms) may be prepared as follows. Commercially available 1-chloro-2-methylpropane may be fluorinated to form 1-chloro-1,2-difluoro-2-methylpropane which may be dehydrohalogenated to form 1-chloro-1-fluoro-2-methylpropene. The 1-chloro-1-fluoro-2-methylpropene may be fluorinated to form 1-chloro-1,1,2-trifluoro-2-methylpropane which may be dehydrohalogenated to form 3-chloro-3,3-difluoro-2-methylpropene. The 3-chloro-3,3-difluoro-2-methylpropene may be fluorinated to form 1-chloro-1,1,2,3-tetrafluoro-2-methylpropane which may be dehydrogenated to form 3-chloro-1,3,3-trifluoro-2-methylpropene. The 3-chloro-1,3,3-trifluoro-2-methylpropene may be fluorinated to form 1-chloro-1,1,2,3,3-pentafluoro-2-methylpropane which may be dehydrohalogenated to form 3-chloro-1,1,3,3-tetrafluoro-2-methylpropene. The 3-chloro-1,1,3,3-tetrafluoro-2-methylpropene may be fluorinated to form 1-chloro-1,1,3,3,3-pentafluoro-2-methylpropane.

$CH_3C(CF_2H)ClCF_3$ (HCFC-355mps) may be prepared as follows. Commercially available 1-chloro-2-methylpropene may be fluorinated to form 1,1,2-trifluoro-2-methylpropane which may be dehydrohalogenated to form 3,3-difluoro-2-methylpropene. The 3,3-difluoro-2-methylpropene may be fluorinated to form 1,1,2,3-tetrafluoro-2-methylpropane which may be dehydrohalogenated to form 1,3,3-trifluoro-2-methylpropene. The 1,3,3-trifluoro-2-methylpropene may be fluorinated to form 1,1,2,3,3-pentafluoro-2-methylpropane which may be dehydrohalogenated to form 1,1,3,3-tetrafluoro-2-methylpropene. The 1,1,3,3-tetrafluoro-2-methylpropene may be chlorinated to form 1,2-dichloro-1,1,4,4,4-tetrafluoro-2-methylpropane which may be fluorinated to form 2-chloro-1,1,1,3,3-pentafluoro-2-methylpropane.

$CH_3C(CFClH)FCF_3$ (HCFC-355mrs) may be prepared as follows. Commercially available 1-chloro-2-methylpropene may be fluorinated to form 1-chloro-1,2-difluoro-2-methylpropane which may be dehydrohalogenated to form 3-chloro-3-fluoro-2-methylpropene. The 3-chloro-3-fluoro-2-methylpropene may be fluorinated to form 1-chloro-1,2,3-trifluoro-2-methylpropane which may be dehydrohalogenated to form 3-chloro-1,3-difluoro-2-methylpropene. The 3-chloro-1,3-difluoro-2-methylpropene may be fluorinated to form 1-chloro-1,2,3,3-tetrafluoro-2-methylpropane which may be dehydrohalogenated to form 3-chloro-1,1,3-trifluoro-2-methylpropene. The 3-chloro-1,1,3-trifluoro-2-methylpropene may be fluorinated to form 1-chloro-1,2,3,3,3-pentafluoro-2-methylpropane.

The preferred branched hydrochlorofluorocarbons having 4 carbon atoms are $CH_3C(CF_3)HCF_2Cl$, $CH_3C(CF_2H)ClCF_3$, and $CH_3C(CFClH)FCF_3$.

The branched hydrochlorofluorocarbons having 5 carbon atoms of the present invention are listed in Table V below. The unit on the calculated $K_{OH}$ is $cm^3/molecule/sec \times 10^{-14}$ and the unit on the calculated lifetime is years in Table V below.

TABLE V

| Number | Chemical Formula | $K_{OH}$ | Lifetime |
|---|---|---|---|
| HCFC-356mlfq | $CFH_2CH_2C(CF_2Cl)FCF_3$ | 12.0 | 0.63 |
| HCFC-357lcsp | $CF_2ClCF_2C(CH_3)FCF_2H$ | 15.1 | 0.50 |
| HCFC-357lsem | $CF_3CFHC(CH_3)FCF_2Cl$ | 14.6 | 0.52 |
| HCFC-357mbsp | $CF_3CFClC(CH_3)FCF_2H$ | 15.0 | 0.50 |
| HCFC-357mcpo | $CF_3CF_2C(CF_2H)HCClH_2$ | 14.7 | 0.51 |
| HCFC-357mcsp | $CF_3CF_2C(CH_3)ClCF_2H$ | 13.7 | 0.55 |
| HCFC-357mcsr | $CF_3CF_2C(CH_3)FCFClH$ | 15.1 | 0.50 |
| HCFC-357mlcs | $CH_3CF_2C(CF_2Cl)HCF_3$ | 10.7 | 0.71 |
| HCFC-357mmbs | $CH_3CFClC(CF_3)HCF_3$ | 9.5 | 0.80 |
| HCFC-357mmel | $CF_2ClCHFC(CH_3)FCF_3$ | 14.3 | 0.53 |
| HCFC-357mmfo | $CH_2ClCH_2C(CF_3)FCF_3$ | 8.8 | 0.86 |
| HCFC-357mmfq | $CFH_2CH_2C(CF_3)ClCF_3$ | 11.5 | 0.66 |
| HCFC-357mmfr | $CFClHCH_2C(CF_3)HCF_3$ | 14.0 | 0.54 |
| HCFC-357mofm | $CF_3CH_2C(CClH_2)FCF_3$ | 14.1 | 0.54 |
| HCFC-357msem | $CF_3CFHC(CH_3)ClCF_3$ | 13.0 | 0.57 |
| HCFC-358mcsr | $CF_3CF_2C(CH_3)FCClFH$ | 13.8 | 0.55 |
| HCFC-366mmds | $CH_3CClHC(CF_3)HCF_3$ | 12.8 | 0.59 |
| HCFC-366mmfo | $CClH_2CH_2C(CF_3)HCF_3$ | 13.2 | 0.57 |
| HCFC-375lcss | $CF_2ClCF_2C(CH_3)FCH_3$ | 10.7 | 0.71 |
| HCFC-375mbss | $CF_3CFClC(CH_3)FCH_3$ | 10.7 | 0.71 |
| HCFC-393less | $CF_2ClCFHC(CH_3)HCH_3$ | 12.1 | 0.62 |
| HCFC-393mdss | $CF_3CClHC(CH_3)HCH_3$ | 10.0 | 0.76 |
| HCFC-393sfms | $CH_3CH_2C(CF_3)ClCH_3$ | 13.0 | 0.58 |
| HCFC-3-11-1rfss | $CFClHCH_2C(CH_3)HCH_3$ | 13.4 | 0.56 |

Known methods for making fluorinated compounds can be modified in order to form the branched hydrochlorofluorocarbons having 5 carbon atoms of the present invention.

$CFH_2CH_2C(CF_2Cl)FCF_3$ (HCFC-356mlfq) may be prepared as follows. Commercially available 1,4-dichloro-2-butene may be reacted with commercially available trifluoromethyl iodide to form 1,4-dichloro-2-trifluoromethyl-3-iodobutane which may be dehydrohalogenated to form 1,4-dichloro-3-trifluoromethyl-1-butene. The 1,4-dichloro-3-trifluoromethyl-1-butene may be hydrogenated to form 1,4-dichloro-2-trifluoromethylbutane which may be fluorinated to form 1-chloro-2-trifluoromethyl-4-fluorobutane. The 1-chloro-2-trifluoromethyl-4-fluorobutane may be dehydrogenated to form 1-chloro-2-trifluoromethyl-4-fluoro-1-butene which may be fluorinated to form 1-chloro-2-trifluoromethyl-1,2,4-trifluorobutane. The 1-chloro-2-trifluoromethyl-1,2,4-trifluorobutane may be dehydrohalogenated to form 1-chloro-2-trifluoromethyl-1,4-difluoro-1-butene which may be fluorinated to form 1-chloro-2-trifluoromethyl-1,1,2,4-tetrafluorobutane.

$CF_3CFHC(CH_3)FCF_2Cl$ (HCFC-357lsem) may be prepared as follows. Commercially available 1,4-dichloro-2-butene may be reacted with commercially available iodomethane to form 1,4-dichloro-3-iodo-2-methylbutane which may be dehydrohalogenated to form 1,4-dichloro-3-methyl-1-butene. The 1,4-dichloro-3-methyl-1-butene may be fluorinated to form 1-chloro-2-methyl-3,4,4-trifluorobutane which may be dehydrohalogenated to form 1,1-difluoro-3-methyl-4-chloro-1-butene. The 1,1-difluoro-3-methyl-4-chloro-1-butene may be fluorinated to form 1-chloro-2-methyl-3,4,4,4-tetrafluorobutane which may be dehydrogenated to form 1-chloro-2-methyl-3,4,4,4-tetrafluoro-1-butene. The 1-chloro-2-methyl-3,4,4,4-tetrafluoro-1-butene may be fluorinated to form 1-chloro-2-methyl-1,2,3,4,4,4-hexafluorobutane which may be dehydrohalogenated to form 1-chloro-2-methyl-1,3,4,4,4-pentafluoro-1-butene. The 1-chloro-2-methyl-1,3,4,4,4-pentafluoro-1-butene may be fluorinated to form 1-chloro-2-methyl-1,1,2,3,4,4,4-heptafluorobutane.

$CF_3CFClC(CH_3)FCF_2H$ (HCFC-357mbsp) may be prepared as follows. Commercially available 2,3-dichlorohexafluoro-2-butene may be reacted with commercially available iodomethane to form 2,3-dichloro-3-iodo-2-methyl-1,1,1,4,4,4-hexafluoropropane which may be fluorinated to form 2-methyl-3-chloro-1,1,1,2,3,4,4-heptafluorobutane. The 2-methyl-3-chloro-1,1,1,2,3,4,4-heptafluorobutane may be dehalogenated to form 3-chloro-2-methyl-1,1,3,4,4,4-hexafluoro-1-butene which may be reacted with commercially available hydrogen fluoride to form 3-chloro-2-methyl-1,1,2,3,4,4,4-heptafluorobutane.

$CF_3CF_2C(CH_3)ClCF_2H$ (HCFC-357mcsp) may be prepared as follows. Commercially available 2,3-dichlorohexafluoro-2-butene may be reacted with iodomethane to form 2-methyl-2,3-dichloro-3-iodo-1,1,1,4,4,4-hexafluorobutane which may be fluorinated to form 2-methyl-1,1,1,2,3,3,4,4,4-nonafluorobutane. The 2-methyl-1,1,1,2,3,3,4,4,4-nonafluorobutane may be dehalogenated to form 2-methyl-1,1,3,3,4,4,4-heptafluoro-1-butene which may be reacted with commercially available hydrogen chloride to form 2-chloro-2-methyl-1,1,3,3,4,4,4-heptafluorobutane.

$CH_3CF_2C(CF_2Cl)HCF_3$ (HCFC-357mlcs) may be prepared as follows. Commercially available 1,3-dichloro-2-butene may be reacted with commercially available trifluoromethyl iodide to form 1,3-dichloro-2-trifluoromethyl-3-iodobutane which may be fluorinated to form 1,3,3-trifluoro-2-trifluoromethylbutane. The 1,3,3-trifluoro-2-trifluoromethylbutane may be dehydrogenated to form 1,3,3-trifluoro-2-trifluoromethyl-1-butene which may be fluorinated to form 1,1,2,3,3-pentafluoro-2-trifluoromethylbutane. The 1,1,2,3,3-pentafluoro-2-trifluoromethylbutane may be dehydrohalogenated to form 1,1,3,3-tetrafluoro-2-trifluoromethyl-1-butene which may be reacted with commercially available hydrogen chloride to form 1-chloro-1,1,3,3-tetrafluoro-2-trifluoromethylbutane.

$CH_3CFClC(CF_3)HCF_3$ (HCFC-357mmbs) may be prepared as follows. Commercially available 2,3-dichlorohexafluoro-2-butene may be reacted with commercially available trifluoromethyl iodide to form 2,3-dichloro-3-iodo-2-trifluoromethyl-1,1,1,4,4,4-hexafluorobutane which may be fluorinated to form 2-trifluoromethyl-1,1,1,2,3,3,4,4,4-nonafluorobutane. The 2-trifluoromethyl-1,1,1,2,3,3,4,4,4-nonafluorobutane may be dehalogenated to form 3-trifluoromethyl-1,1,2,3,4,4,4-heptafluoro-1-butene which may be hydrogenated to form 2-trifluoromethyl-1,1,1,2,3,4,4-heptafluorobutane. The 2-trifluoromethyl-1,1,1,2,3,4,4-heptafluorobutane may be dehydrohalogenated to form 3-trifluoromethyl-1,2,3,4,4,4-hexafluoro-1-butene which may be hydrogenated to form 3-trifluoromethyl-1,2,3,4,4,4-hexafluorobutane. The 3-trifluoromethyl-1,2,3,4,4,4-hexafluorobutane may be dehydrohalogenated to form 3-trifluoromethyl-2,3,4,4,4-pentafluoro-1-butene which may be reacted with commercially available hydrogen chloride to form 3-chloro-2-trifluoromethyl-1,1,1,2,3-pentafluorobutane. The 3-chloro-2-trifluoromethyl-1,1,1,2,3-pentafluorobutane may be dehalogenated to form 3-chloro-2-trifluoromethyl-1,1,3-trifluoro-1-butene which may be reacted with commercially available hydrogen fluoride to form 3-chloro-2-trifluoromethyl-1,1,1,3-tetrafluorobutane.

$CF_2ClCHFC(CH_3)FCF_3$ (HCFC-357mmel) may be prepared as follows. Commercially available 2,3-dichlorohexafluoro-2-butene may be reacted with commercially available iodomethane to form 2,3-dichloro-3-iodo-1,1,1,4,4,4-hexafluoro-2-methylbutane which may be fluorinated to form 2-methylperfluorobutane. The 2-methylperfluorobutane may be dehalogenated to form 1,1,2,3,4,4,4-heptafluoro-3-methyl-1-butene which may be reacted with commercially available hydrogen chloride to form 4-chloro-1,1,1,2,3,4,4-heptafluoro-2-methylbutane.

The method of R. N. Haszeldine et al., supra, can be modified to form $CH_2ClCH_2C(CF_3)FCF_3$ (HCFC-357mmfo) as follows. Commercially available perfluoroisopropyl iodide may be reacted with commercially available ethylene to prepare 2-trifluoromethyl-1,1,1,2-tetrafluoro-4-iodobutane which may then be chlorinated to form 2-trifluoromethyl-1,1,1,2-tetrafluoro-4-chlorobutane.

$CFH_2CH_2C(CF_3)ClCF_3$ (HCFC-357mmfq) may be prepared as follows. Commercially available 2,3-dichlorohexafluoro-2-butene may be reacted with commercially available trifluoromethyl iodide to form 2,3-dichloro-3-iodo-1,1,1,4,4,4-hexafluoro-2-trifluoromethylbutane which may be fluorinated to form 2-chloro-2-trifluoromethyl-perfluorobutane. The 2-chloro-2-trifluoromethyl-perfluorobutane may be dehalogenated to form 3-chloro-3-trifluoromethyl-1,1,2,4,4,4-hexafluoro-1-butene which may be hydrogenated to form 2-chloro-2-trifluoromethyl-1,1,1,3,4,4-hexafluorobutane. The 2-chloro-2-trifluoromethyl-1,1,1,3,4,4-hexafluorobutane may be fluorinated to form 3-chloro-3-trifluoromethyl-1,4,4,4-tetrafluoro-1-butene which may then be hydrogenated to form 2-chloro-2-trifluoromethyl-1,1,1,4-tetrafluorobutane.

$CF_3CFHC(CH_3)ClCF_3$ (HCFC-357msem) may be prepared as follows. Commercially available 2,3-dichlorohexafluoro-2-butene may be reacted with commercially available iodomethane to form 2,3-dichloro-3-iodo-1,1,1,4,4,4-hexafluoro-2-methylbutane which may be chlorinated to form 2,3,3-trichloro-1,1,1,4,4,4-hexafluoro-2-methylbutane. The 2,3,3-trichloro-1,1,1,4,4,4-hexafluoro-2-methylbutane may be dehalogenated to form 3-chloro-1,1,1,4,4,4-hexafluoro-2-methyl-2-butene which may be reacted with commercially available hydrogen fluoride to form 3-chloro-1,1,1,3,4,4,4-heptafluoro-2-methylbutane. The 3-chloro-1,1,1,3,4,4,4-heptafluoro-2-methylbutane may be dehydrohalogenated to form 1,1,1,4,4,4-hexafluoro-2-methyl-2-butene which may be reacted with commercially available hydrogen chloride to form 2-chloro-1,1,1,3,4,4,4-heptafluoro-2-methylbutane.

$CF_3CF_2C(CH_3)FCClFH$ (HCFC-358mcsr) may be prepared as follows. Commercially available 2,3-dichlorohexafluoro-2-butene may be reacted with commercially available trifluoromethyl iodide to form 2,3-dichloro-3-iodo-1,1,1,4,4,4-hexafluoro-2-methylbutane which may be fluorinated to form 2-methyl-perfluorobutane. The 2-methyl-perfluorobutane may be dehalogenated to form 2-methyl-perfluoro-1-butene which may be reacted with commercially available hydrogen fluoride to form 1,1,2,3,3,4,4,4-octafluoro-2-methylbutane. The 1,1,2,3,3,4,4,4-octafluoro-2-methylbutane may be dehalogenated to form 1,3,3,4,4,4-hexafluoro-2-methyl-1-butene which may be chlorinated to form 1,2-dichloro-1,3,3,4,4,4-hexafluoro-2-methylbutane. The 1,2-dichloro-1,3,3,4,4,4-hexafluoro-2-methylbutane may be dehydrohalogenated to form 1-chloro-1,3,3,4,4,4-hexafluoro-2-methyl-1-butene which may be reacted with commercially available hydrogen fluoride to form 1-chloro-1,2,3,3,4,4,4-heptafluoro-2-methylbutane.

$CH_3CClHC(CF_3)HCF_3$ (HCFC-366mmds) may be prepared as follows. Commercially available 2,3-dichlorohexafluoro-2-butene may be reacted with trifluoromethyl iodide to form 2,3-dichloro-3-iodo-1,1,1,4,4,4-hexafluoro-2-trifluoromethylbutane which may be chlorinated to form 3-iodo-1,1,1,4,4,4-hexafluoro-2-methyl-2-butene. The 3-iodo-1,1,1,4,4,4-hexafluoro-2-trifluoromethyl-2-butene may be hydrogenated to form 3-iodo-1,1,1,4,4,4-hexafluoro-2-trifluoromethylbutane which may be dehydrohalogenated to form 2-iodo-1,1,4,4,4-pentafluoro-3-trifluoromethyl-1-butene. The 2-iodo-1,1,4,4,4-pentafluoro-3-trifluoromethyl-1-butene may be hydrogenated to form 3-iodo-1,1,1,4,4-pentafluoro-2-trifluoromethylbutane which may be chlorinated to form 3-chloro-1,1,1,4,4-pentafluoro-2-trifluoromethylbutane. The 3-chloro-1,1,1,4,4-pentafluoro-2-trifluoromethylbutane may be dehydrohalogenated to form 2-chloro-1,4,4,4-tetrafluoro-3-trifluoromethyl-1-butene which may be hydrogenated to form 3-chloro-1,1,1,4-tetrafluoro-2-trifluoromethylbutane. The 3-chloro-1,1,1,4-tetrafluoro-2-trifluoromethylbutane may be dehydrohalogenated to form 2-chloro-4,4,4-trifluoro-3-trifluoromethyl-1-butene which may be hydrogenated to form 3-chloro-1,1,1-trifluoro-2-trifluoromethylbutane.

The preferred branched hydrochlorofluorocarbons having 5 carbon atoms are $CFH_2CH_2C(CF_2Cl)FCF_3$, $CF_3CFHC(CH_3)FCF_2Cl$, $CF_3CFClC(CH_3)FCF_2H$, $CF_3CF_2C(CH_3)ClCF_2H$, $CH_3CF_2C(CF_2Cl)HCF_3$, $CH_3CFClC(CF_3)HCF_3$, $CF_2ClCHFC(CH_3)FCF_3$, $CH_2ClCH_2C(CF_3)FCF_3$, $CFH_2CH_2C(CF_3)ClCF_3$, $CF_3CFHC(CH_3)ClCF_3$, $CF_3CF_2C(CH_3)FCClFH$, and $CH_3CClHC(CF_3)HCF_3$.

Other advantages of the invention will become apparent from the following description.

DETAILED DESCRIPTION OF THE PREFERRED EMBODIMENTS

Known solvents may be blended with the hydrochlorofluorocarbons of the present invention. Examples of useful known solvent are listed in Table VI below.

TABLE VI

| Number | Chemical Formula |
| --- | --- |
| HCFC-234cc | $CF_2ClCF_2CClH_2$ |
| HCFC-234cd | $CH_2FCF_2CFCl_2$ |
| HCFC-244ca | $CF_2HCF_2CClH_2$ |
| HCFC-244cb | $CFH_2CF_2CFClH$ |
| HCFC-253ca | $CFH_2CF_2CClH_2$ |
| HCFC-253cb | $CH_3CF_2CFClH$ |

HCFC-234cc may be formed by any known method such as the reaction of 1,1,1,2,2,3-hexachloropropane with antimony pentachloride and hydrogen fluoride at 100° C. HCFC-234cd may be formed by any known method such as the reaction of 1,1,1-trichloro-2,2,3-trifluoropropane with antimony pentachloride and hydrogen fluoride at 120° C.

HCFC-244ca may be formed by any known method such as the reaction of 1,1,2,2,3-pentachloropropane with antimony pentachloride and hydrogen fluoride at 100° C. HCFC-244cb may be formed by any known method such as the reaction of 1-chloro-1,1,2,2-tetrafluoropropane with cesium fluoride and tetrabutylammonium bromide at 150° C.

HCFC-253ca may be formed by any known method such as the reaction of 1,2,3-trichloro-2-fluoropropane with niobium pentachloride and hydrogen fluoride at 100° C. HCFC-253cb may be formed by any known method such as the reaction of 1,1,2,2-tetrachloropropane with tantalum pentafluoride and hydrogen fluoride at 130° C.

The present hydrochlorofluorocarbons may be used as solvents in vapor degreasing, solvent cleaning, cold cleaning, dewatering, dry cleaning, defluxing, decontamination, spot cleaning, aerosol propelled rework, extraction, particle removal, and surfactant cleaning applications. In these uses, the object to be cleaned is immersed in one or more stages in the liquid and/or vaporized solvent or is sprayed with the liquid solvent. Elevated temperatures, ultrasonic energy, and/or agitation may be used to intensify the cleaning effect.

The present hydrochlorofluorocarbons are also useful as blowing agents, Rankine cycle and absorption refrigerants, and power fluids and especially as refrigerants for centrifugal refrigeration chillers.

The present invention is more fully illustrated by the following non-limiting Examples.

COMPARATIVES

The hydrochlorofluorocarbons having 3 carbon atoms and 1 or 2 chlorine atoms in Table VII below are isomers of the compounds of the present invention. As discussed above, these compounds have OH rate constants which are less than 8 cm$^3$/molecule/sec×10$^{-14}$ or greater than 25 cm$^3$/molecule/sec×10$^{-14}$. The unit on the K$_{OH}$ is cm$^3$/molecule/sec×10$^{-14}$ and the unit on the lifetime is years in Table VII below.

TABLE VII

| Number | Chemical Formula | K$_{OH}$ | Lifetime |
|---|---|---|---|
| HCFC-243eb | CF$_2$HCFHCCl$_2$H | 31.3 | 0.24 |
| HCFC-243ed | CCl$_2$FFHCFH$_2$ | 30.0 | 0.25 |
| HCFC-244bb | CF$_3$CFClCH$_3$ | 1.8 | 4.20 |
| HCFC-252aa | CFH$_2$CCl$_2$CFH$_2$ | 49.33 | 0.15 |
| HCFC-252ab | CH$_3$CCl$_2$CF$_2$H | 34.14 | 0.22 |
| HCFC-252ea | CClH$_2$CFHCClFH | 31.8 | 0.24 |
| HCFC-252eb | CFH$_2$CFHCCl$_2$H | 39.57 | 0.19 |
| HCFC-262fc | CF$_2$ClCH$_2$CH$_3$ | 2.9 | 2.61 |
| HCFC-271fa | CFH$_2$CH$_2$CClH$_2$ | 35.8 | 0.21 |

EXAMPLES 1-85

Each solvent listed in Tables II through V is added to mineral oil in a weight ratio of 50:50 at 27° C. Each solvent is miscible in the mineral oil.

Having described the invention in detail and by reference to preferred embodiments thereof, it will be apparent that modifications and variations are possible without departing from the scope of the invention defined in the appended claims.

What is claimed is:

1. A hydrochlorofluorocarbon having an OH rate constant between about 8 and about 25 cm$^3$/molecule/sec×10$^{-14}$ selected from the group consisting of CFH$_2$CFClCF$_2$H, CF$_2$HCFHCFClH, CF$_3$CFHCClH$_2$, CFH$_2$CFHCF$_2$Cl, and CFClHCH$_2$CF$_3$.

2. The hydrochlorofluorocarbon of claim 1 wherein said hydrochlorofluorocarbon is CFH$_2$CFClCF$_2$H, CFH$_2$CFHCF$_2$Cl, or CFClHCH$_2$CF$_3$.

3. The hydrochlorofluorocarbon of claim 1 wherein said hydrochlorofluorocarbon is CFH$_2$CFClCF$_2$H.

4. The hydrochlorofluorocarbon of claim 1 wherein said hydrochlorofluorocarbon is CFH$_2$CFHCF$_2$Cl.

5. The hydrochlorofluorocarbon of claim 1 wherein said hydrochlorofluorocarbon is CFClHCH$_2$CF$_3$.

6. A composition comprising one or more hydrochlorofluorocarbons selected from the group consisting of CFH$_2$CFClCF$_2$H, CF$_2$HCFHCFClH, CF$_3$CFHCClH$_2$, CFH$_2$CFHCF$_2$Cl, and CFClHCH$_2$CF$_3$, and one or more hydrochlorofluorocarbons selected from the group consisting of CF$_2$ClCF$_2$CClH$_2$, CH$_2$FCF$_2$CFCl$_2$, CF$_2$HCH$_2$CClH$_2$, CFH$_2$CF$_2$CFClH, CFH$_2$CF$_2$CClH$_2$, and CH$_3$CF$_2$CFClH.

* * * * *

UNITED STATES PATENT AND TRADEMARK OFFICE
CERTIFICATE OF CORRECTION

PATENT NO.   : 5,316,690
DATED        : May 31, 1994
INVENTOR(S)  : Li

It is certified that error appears in the above-identified patent and that said Letters Patent is hereby corrected as shown below:

Column 1,
Line 15, "25 cm$^3$/molecule/sec x 10-14" should read -- 25 cm$^3$/molecule/sec x $10^{-14}$ --.

Column 2,
Line 12, delete "470" and insert -- 47 -- therefor.
Line 16, delete "630" and insert -- 63 -- therefor.
Line 56, "cm$^3$/molecule/sec x 10-14" should read -- cm$^3$/molecule/sev x $10^{-14}$ -- .

Column 3,
Line 40, "25 cm$^3$/molecule/sec x $10^{31\ 14}$" should read -- 25 cm$^3$/molecule/sec x $10^{-14}$ -- .
Line 45, "*Rey.*" should read -- *Rev.* -- .

Column 4,
Line 21, before "unexpected", insert -- was -- .

Column 5,
Line 67, "1-fluoro 1-propene" should read -- 1- fluoro-1-propene -- .

Column 8,
Line 7, "cm$^3$/molecule/sec x $10^{31\ 14}$" should read -- cm$^3$/molecule/sec x $10^{-14}$ -- .
Line 25, "methylpropane" should read -- methylpropene -- .

Column 14,
Line 4, "CCl$_2$FFHCFH$_2$" should read -- CCl$_2$CFHCFH$_2$ -- .

UNITED STATES PATENT AND TRADEMARK OFFICE
CERTIFICATE OF CORRECTION

PATENT NO. : 5,316,690
DATED : May 31, 1994
INVENTOR(S) : Li

Page 2 of 2

It is certified that error appears in the above-identified patent and that said Letters Patent is hereby corrected as shown below:

Claim 1,
Line 3, "sec x $10^{-}$" should read -- sec x $10^{-14}$ -- .

Claim 6,
Line 7, "$CF_2HCH_2CClH_2$" should read -- $CF_2HCF_2CClH_2$ -- .

Signed and Sealed this

Twenty-first Day of August, 2001

Attest:

*Nicholas P. Godici*

NICHOLAS P. GODICI
*Attesting Officer*     *Acting Director of the United States Patent and Trademark Office*